United States Patent
Garcia-Rodenas et al.

(10) Patent No.: US 11,517,579 B2
(45) Date of Patent: Dec. 6, 2022

(54) COMPOSITIONS COMPRISING AT LEAST ONE N-ACETYLATED AND AT LEAST ONE FUCOSYLATED OLIGOSACCHARIDE FOR USE IN THE PROMOTION OF DIGESTIVE CAPACITY IN INFANTS AND YOUNG CHILDREN

(71) Applicant: SOCIETE DES PRODUITS NESTLE S.A., Vevey (CH)

(72) Inventors: Clara Lucia Garcia-Rodenas, Forel (CH); Jose Manuel Ramos Nieves, Lausanne (CH); Myriam Sandrine Steinmann, Echallens (CH)

(73) Assignee: Societe des Produits Nestle S.A., Vevey (CH)

( * ) Notice: Subject to any disclaimer, the term of this patent is extended or adjusted under 35 U.S.C. 154(b) by 144 days.

(21) Appl. No.: 16/955,495

(22) PCT Filed: Dec. 20, 2018

(86) PCT No.: PCT/EP2018/086279
§ 371 (c)(1),
(2) Date: Jun. 18, 2020

(87) PCT Pub. No.: WO2019/122178
PCT Pub. Date: Jun. 27, 2019

(65) Prior Publication Data
US 2020/0360407 A1 Nov. 19, 2020

(30) Foreign Application Priority Data
Dec. 21, 2017 (EP) .................. 17209456

(51) Int. Cl.
*A61K 31/702* (2006.01)
*A23L 33/125* (2016.01)
*A23L 33/00* (2016.01)
*A61K 45/06* (2006.01)

(52) U.S. Cl.
CPC .......... *A61K 31/702* (2013.01); *A23L 33/125* (2016.08); *A23L 33/40* (2016.08); *A61K 45/06* (2013.01)

(58) Field of Classification Search
None
See application file for complete search history.

(56) References Cited

U.S. PATENT DOCUMENTS

| | | | |
|---|---|---|---|
| 2004/0115179 A1* | 6/2004 | Liu | A61P 1/14 424/93.45 |
| 2014/0286908 A1 | 9/2014 | Garcia-Rodenas et al. | |
| 2018/0036327 A1* | 2/2018 | McConnell | A61K 31/702 |
| 2018/0153915 A1* | 6/2018 | Morrow | A23L 29/30 |
| 2018/0228195 A1* | 8/2018 | Thakkar | A23L 33/40 |

FOREIGN PATENT DOCUMENTS

| | | |
|---|---|---|
| WO | 2013025104 | 2/2013 |
| WO | 2016176484 | 11/2016 |

OTHER PUBLICATIONS

Hu, L., Peng, X., Chen, H., Yan, C., Liu, Y., Xu, Q., . . . & Che, L. (2017). Effects of intrauterine growth retardation and Bacillus subtilis PB6 supplementation on growth performance, intestinal development and immune function of piglets . . . European journal of nutrition, 56(4),1753-1765. (Year: 2017).*

DeSesso, J. M., & Jacobson, C. F. (2001). Anatomical and physiological parameters affecting gastrointestinal absorption in humans and rats. Food and chemical toxicology, 39(3), 209-228. (Year: 2001).*

Lindquist et al. "Lipid digestion and absorption in early life: an update" Curr Opin Clin Nutr Metab Care, 2010, vol. 13, pp. 314-320.

Jantscher-Krenn et al. "Human milk oligosaccharides and their potential benefits for the breast-fed neonate" Minerva Pediatr, 2012, vol. 63, pp. 83-99.

Landberg et al. "Changes in Glycosylation of Human Bile-Salt-Stimulated Lipase during Lactation" Archives of Biochemistry and Biophysics, 2000, vol. 377, No. 2, pp. 246-254.

Kunz et al. "Oligosaccharides in Human Milk: Structural, Functional, and Metabolic Aspects" Annu. Rev. Nutr., 2000, vol. 20, pp. 699-722.

Holscher et al. "Human Milk Oligosaccharides Influence Maturation of Human Intestinal Caco-2Bbe and HT-29 Cell Lines" The Journal of Nutrition, 2014, vol. 144, pp. 586-591.

* cited by examiner

*Primary Examiner* — Dale R Miller
(74) *Attorney, Agent, or Firm* — K&L Gates LLP

(57) ABSTRACT

This invention relates to compositions for use in the promotion of the development and/or of the growth of the surface area of the small intestine and in the associated improvement of the digestive capacity in an infant or in a young child.

19 Claims, 1 Drawing Sheet

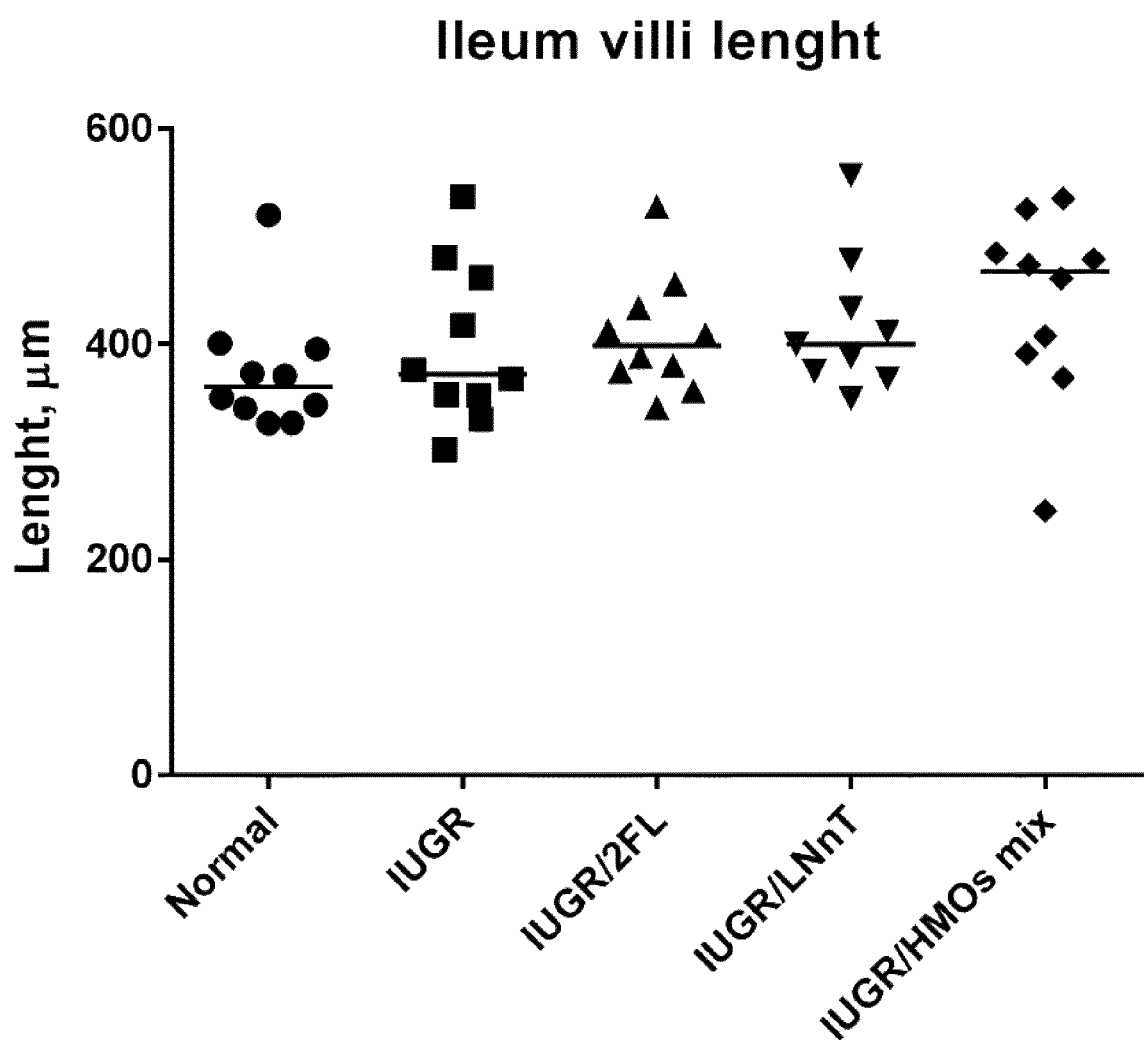

COMPOSITIONS COMPRISING AT LEAST ONE N-ACETYLATED AND AT LEAST ONE FUCOSYLATED OLIGOSACCHARIDE FOR USE IN THE PROMOTION OF DIGESTIVE CAPACITY IN INFANTS AND YOUNG CHILDREN

CROSS REFERENCE TO RELATED APPLICATIONS

The present application is a National Stage of International Application No. PCT/EP2018/086279, filed on Dec. 20, 2018, which claims priority to European Patent Application No. 17209456.7, filed on Dec. 21, 2017, the entire contents of which are being incorporated herein by reference.

FIELD OF THE INVENTION

This invention relates to compositions for use in the promotion of the development and/or of the growth of the surface area of the small intestine and in the associated improvement of the digestive capacity in an infant or in a young child.

BACKGROUND OF THE INVENTION

Development of the intestine in infants and in young children is key for the infant and for the child development in particular it is very important for the infant or young child to have optimal digestive capacity. It is therefore desirable to develop compositions promoting the development of the digestive capacity in infants and young children.

In the case of proteins and carbohydrates, these are first digested to smaller fragments in the gut lumen then they are further digested into amino acids, di- and tri-peptides and monosaccharides, by a variety of enzymes sitting in the apical side of the small intestinal enterocytes, before being absorbed by the body.

Like proteins and carbohydrates, dietary lipids and liposoluble vitamins are hydrolysed in the gut lumen by different types of lipases. After a first step of digestion in the stomach by gastric lipase, large droplets of undigested fat and fat digestion products enter the intestine, where they are mixed with bile salts to form a fine emulsion readily accessible to the pancreatic lipases.

Lipid digestion products are then further incorporated into bile salt micelles in the lumen and form the so-called mixed micelles. This process remarkably increases the solubility of the lipid digestion products, which, in turn, strongly facilitates their absorption by the enterocytes. A minimum concentration of bile salts, called critical micellar concentration, is required in the lumen to the formation of bile salt micelles. In healthy adults, the luminal concentration of bile salts during the postprandial state is above the critical micellar concentration, which ensures a highly efficient lipid digestion and absorption. In infants, particularly preterm infants (see Lindqvist et al., Lipid digestion and absorption in early life: an update, Current Opinion in Clinical Nutrition and Metabolic Care; 13(2010): 314-320), and in some disease states (ex. cystic fibrosis), the luminal concentration of bile salts is low, below the critical micellar concentration, which results in an inefficient lipid digestion and absorption.

A primary consequence of such inefficient lipid digestion is loss of nutrients in the faeces, namely loss of liposoluble vitamins and fat, such as essential fatty acids and LC-PUFA, as well as loss of associated energy. Such nutrients and energy are thus not available for infant growth and development. In addition, such inefficient digestion is associated with diarrhoea, feeding intolerance and alterations in the intestinal microbiota, for example. It is thus particularly desirable to find solutions to improve digestion in infants and young children, and in particular in preterm or low birth weight infants.

The bile salts in the intestinal lumen transit along the small intestine and are efficiently absorbed (up to 95%) in the ileum of healthy adults. The spared bile salts are recirculated via the portal vein into the liver, where they are taken up for secretion again into the intestinal lumen. Therefore, most of luminal bile salt pool is dependent of this entero-hepatic circulation, and only a small proportion results from de novo synthesis. The entero-hepatic circulation process is however defective in young infants (see Belle et al.; Intestinal absorption of bile salts: immature development in the neonate; J Pediatr 94 (1979): 472-476), particularly in preterm infants and in certain disease states like short bowel syndrome. In particular, increase in the ileal surface of absorption can improve enterohepatic circulation of bile salts, reutilization by the liver and increased luminal bile salt pool resulting in better fat and liposoluble vitamin digestion.

The small intestine plays a critical role in such digestion process. One important parameter influencing the digestive capacity is the morphology of the small intestine. The surface area of the small intestine epithelium, is a key parameter (See Helander et al.; *Surface area of the digestive tract—revisited*; Scandinavian Journal of Gastroenterology; 49 (2014): 681-689). The larger the surface area of the epithelium, the higher the pool of bile salts and digestive enzymes available for final digestion of nutrients such as lipids, liposoluble vitamins, carbohydrates and proteins. Increasing the villi length in the small intestine induces a favourable increase of the surface area and associated improved digestion of macronutrients such as lipids, liposoluble vitamins, proteins and carbohydrates. Such effect of villi length and associated increase of the surface area of the small intestine on the digestive capacity is well documented in the literature. For example the review of L. Montagne et al., *A review of interactions between dietary fibre and the intestinal mucosa, and their consequences on digestive health in young non-ruminant animals*, Animal Feed Science and Technology 108 (2003) p. 95-117, and in particular paragraph 4.3 on page 105, cite several studies highlighting the positive impact of increasing the villi length on the digestive capacity of animals.

It is desirable to improve the digestive capacity in all infants and young children. However, some specific populations of infants and young children are particularly in need of compositions able to promote their development in general and in particular their digestive and/or absorptive capacity. Such infants and young children are for example preterm infants, low birth weight infant, infants and young children suffering from short bowel syndrome and/or growth-retarded infants or young children, and in particular intrauterine growth retarded (IUGR) infants.

Many attempts have been made to develop the digestive capacity in infants and young children, as well as in young animals. In particular, several studies have assessed the impact of diverse types of fibres on the intestinal morphology and on the digestive capacity of young animals, infants or young children. The above-mentioned review of L. Montagne et al. cites diverse studies showing variable effect of different types of dietary fibres, some being associated with positive effects on digestive capacity, while others appeared detrimental.

One example of a study where dietary fibre has shown a positive effect is P. Liu and al, *Effects of chito-oligosaccharide supplementation on the growth performance, nutrient digestibility*, intestinal morphology, and fecal shedding of *Escherichia coli* and *Lactobacillus* in weaning pigs, J. Anim. Sci. 86 (2008), p. 2609-2618. In this study an increase of the villus height and villus:crypt ratio in the ileum and jejunum was associated with increased digestibility in weaning pigs upon supplementation of the pigs diet with chito-oligosaccharides, compared to a control diet. To the contrary, the study of van Meer et al.; *Prebiotic oligosaccharides and the enterohepatic circulation of bile salts in rats;* Am J Physiol Gastrointest Liver Physiol 294 (2008): G540-G547, has shown that supplementation of rat pups diet with galactooligosaccharides did not contribute to a larger bile salt pool size or altered bile salt pool kinetics, and thus was not successful in promoting digestion of fat.

Other ingredients have been assessed for their ability to promote digestion. For example, WO 2011/65552 describes a composition comprising a hydrolysate of a protein from fermented milk (e.g. from cheese), lipids and isomaltulose which was effective in increasing the villi length in the small intestine. Such compositions are however not suitable for infants and young children, as isomaltulose is not desirable to be used in such compositions.

It would be particularly advantageous to identify ingredients specially adapted to human infants and/or young children and capable of improving the digestive capacity of such infants and/or young children.

Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients.

There is clearly a need for developing suitable methods to increase the capacity to digest macronutrients such as lipids, liposoluble vitamins, proteins and/or carbohydrates in infants and young children.

There is also a need to deliver such health benefits in a manner that is particularly suitable for the young subjects (infants and young children), in a manner that does not involve a classical pharmaceutical intervention as these infants or young children are particularly fragile.

There is a need to deliver such health benefits in these infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

There is thus clearly a need to develop alternative methods than the classical pharmaceutical intervention such as the use of antibiotics, at least because of the associated risk of antibiotic resistance development.

SUMMARY OF THE INVENTION

The present inventors have found that a composition comprising at least one fucosylated oligosaccharide and at least one N-acetylated oligosaccharide can advantageously be used to promote the digestive capacity, preferably the capacity to digest fat, liposoluble vitamins, proteins and carbohydrates, in an infant or a young child.

Without wishing to be bound by theory it is believed that these oligosaccharides act synergistically for these specific health conditions.

Accordingly, the present invention therefore provides a nutritional composition comprising at least one fucosylated oligosaccharide and at least one N-acetylated oligosaccharide, for use in a method of promoting the digestive capacity in an infant or a young child.

The present invention also provides a growing-up milk comprising at least one fucosylated oligosaccharide and at least one N-acetylated oligosaccharide, for use in a method of promoting the digestive capacity in a child.

The nutritional composition, respectively the growing up milk, of the present invention is in particular advantageous for use in a method of improving the enterohepatic circulation, in particular the enterohepatic circulation of bile salts, and promoting an increase of the surface area in the small intestine; and promoting an increase of the villi length in the small intestine of an infant or a young child, respectively of a child.

In a particularly advantageous embodiment, the nutritional composition, respectively the growing-up milk, comprises 2'-fucosyllactose (2-FL) and lacto-N-neotetraose (LNnT).

BRIEF DESCRIPTION OF THE FIGURES

FIG. 1 represents the length of the villi in the following groups of young rats:

animals having normal in utero growth (Normal Group; positive control)

animals that have experienced in utero growth retardation and were fed a normal diet (IUGR Group; negative control), animals with in-utero growth retardation having a diet supplemented with 2-FL (IUGR/2FL test group), animals with in-utero growth retardation having a diet supplemented with LNnT (IUGR/LNnT test group), animals with in-utero growth retardation having a diet supplemented with a combination of 2-FL and LNnT (IUGR/HMOs mix test group).

The mean villi length of each group of rats is represented by a horizontal line. The 2-FL and the LNnT groups showed no significant difference with the IUGR group. In contrast, the 2-FL and LNnT group shows significantly longer villi than the other groups. A synergy can therefore be observed between 2-FL and LNnT.

DETAILED DESCRIPTION OF THE INVENTION

As used herein, the following terms have the following meanings.

The term "infant" means a child under the age of 12 months. The expression "young child" means a child aged between one and less than three years, also called toddler. The expression "child" means a between three and seven years of age.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 37 weeks of gestation.

An "infant having a low birth weight" means a new born having a body weight below 2500 g (5.5 pounds) either because of preterm birth or restricted fetal growth. It therefore encompasses:
- infant or young child who has/had a body weight from 1500 to 2500 g at birth (usually called "low birth weight" or LBW)
- infant or young child who has/had a body weight from 1000 to 1500 g at birth (called "very low birth weight" or VLBW)
- infant or young child who has/had a body weight under 1000 g at birth (called "extremely low birth weight" or ELBW).

An "infant born small for gestational age (SGA)" means a baby with birth weights below the $10^{th}$ percentile for babies of the same gestational age.

The expression "nutritional composition" means a composition which nourishes a subject. This nutritional composition is usually to be taken orally or intravenously, and it usually includes a lipid or fat source and a protein source.

In a particular embodiment the composition of the present invention is a hypoallergenic nutritional composition. The expression "hypoallergenic nutritional composition" means a nutritional composition which is unlikely to cause allergic reactions.

In a particular embodiment the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-based drink generally with added vitamins and minerals, that is intended for young children or children.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "days/weeks/months/years of life" and "days/weeks/months/years of birth" can be used interchangeably.

The expression "promoting the digestive capacity" encompasses one or several of the following:
- increasing the surface area of the small intestine, and in particular of the ileum;
- increasing the villi length in the small intestine, in particular in the ileum; and
- improving the enterohepatic circulation, in particular the enterohepatic circulation of bile salts.

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyl-lacto-N-neohexaose, difucosyllacto-N-hexaose I, difucosyl-lacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and without to be bound by theory, this is believed to therefore reduce the risk of infections/inflammations, and particularly the risk of LRT/ear infections and/or inflammations. In addition, the fucosylated oligosaccharides are thought to boost growth and metabolic activity of specific commensal microbes reducing inflammatory response and creating an environment unfavourable for pathogens thus leading to colonization resistance.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the LRT and/or ear infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are lacto-N-neotetraose (LNnT), lacto-N-tetraose (LNT), para-lacto-N-neohexaose (para-LNnH), disialyllacto-N-tetraose (DSLNT) or any combination thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or a growing-up milk or an infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics*. J Nutr. 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising at least one fucosylated oligosaccharide and at least one N-acetylated oligosaccharide, for use in promoting the digestive capacity in an infant or a young child.

A second object of the present invention is a growing-up milk comprising at least one fucosylated oligosaccharide and at least one N-acetylated oligosaccharide, for use in promoting the digestive capacity in a child.

Preferably, the nutritional composition, respectively the growing-up milk, of the present invention is for use in promoting the capacity to digest fat, liposoluble vitamins, proteins and carbohydrates in an infant or a young child, respectively in a child.

To achieve such benefits, the nutritional composition, respectively the growing-up milk, of the invention is preferably for use in a method of
- increasing the surface area of the small intestine, preferably of the ileum;
- increasing the villi length in the small intestine, preferably in the ileum; and
- improving the enterohepatic circulation, in particular the enterohepatic circulation of bile salts;

in an infant or a young child, respectively in a child.

The nutritional composition, respectively the growing-up milk, of the present invention comprises at least one fucosylated oligosaccharide. There can be one or several types of fucosylated oligosaccharide(s). The fucosylated oligosaccharide(s) can indeed be selected from the list comprising 2'-fucosyllactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose, difuco-lacto-N-neohexaose, difucosyllacto-N-neohexaose, fucosyl-para-Lacto-N-hexaose and any combination thereof.

In a preferred embodiment, the nutritional composition, respectively the growing-up milk, according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition or growing-up milk of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The nutritional composition or the growing-up milk of the present invention also comprises at least one the N-acetylated oligosaccharide. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), lacto-N-tetraose (LNT), para-lacto-N-neohexaose (para-LNnH), disialyllacto-N-tetraose (DSLNT) or any combination thereof. In some particular embodiments the N-acetylated oligosaccharide is LNnT. In some particular embodiments the N-acetylated oligosaccharide is LNT. In some other particular embodiments the N-acetylated oligosaccharide is a mixture of LNT and LNnT. In some particular embodiments the nutritional composition or the growing-up milk comprises both LNT and LNnT in a ratio LNT:LNnT between 5:1 and 1:2, or from 2:1 to 1:1, or from 2:1.2 to 2:1.6.

In a preferred embodiment, the nutritional composition or the growing-up milk according to the invention comprises lacto-N-neotetraose (LNnT). In a particular embodiment, there is no other type of N-acetylated oligosaccharide than lacto-N-neotetraose (LNnT), i.e. the nutritional composition or the growing-up milk of the invention comprises only lacto-N-neotetraose (LNnT) as N-acetylated oligosaccharide.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

In a particularly advantageous embodiment of the present invention, the nutritional composition or the growing-up milk comprises 2'-fucosyllactose (2FL) and lacto-N-neotetraose (LNnT).

In another specific embodiment, the nutritional composition or the growing-up milk of the present invention comprises an oligosaccharide mixture that consists of 2'-fucosyllactose (2-FL) and lacto-N-neotetraose (LNnT). In other words, the nutritional composition or the growing-up milk of the invention comprises only 2'-fucosyllactose (2-FL) as fucosylated oligosaccharide and only lacto-N-neotetraose (LNnT) as N-acetylated oligosaccharide.

In a particularly advantageous embodiment of the present invention, the fucosylated oligosaccharide(s) and N-acetylated oligosaccharide(s) are present in the nutritional composition or the growing-up milk in some particular amounts. The term "amount" refers to the total amount of each of these two components in the nutritional composition or the growing-up milk unless otherwise specified. It therefore does not refer to an individual amount except when there is a single type of these components (in that case both the total and individual amounts equal). By way of illustrative example, if there is only one (i.e. only one type of) fucosylated oligosaccharide in the composition (e.g. 2FL), its individual amount (and therefore the total amount of fucosylated oligosaccharides) will be in the range 0.75-1.65 g/L. If there are several (i.e. several types of) fucosylated oligosaccharides, their individual amount will be lower (e.g. if there are 2 different types of fucosylated oligosaccharide, e.g. 2FL+3FL, there may be for example each in an individual amount of 0.5 g/L) but the total amount of fucosylated oligosaccharides will be in the range 0.75-1.65 g/L.

The fucosylated oligosaccharide(s) can be in the nutritional composition or the growing-up milk according to the present invention in a total amount of 0.75-1.65 g/L of the composition. In some embodiments, the fucosylated oligosaccharide(s) may be in a total amount of 0.005-5 g/L of the composition, such as 0.01-3 g/L or 0.02-2 g/L or 0.1-2.5 g/L or 0.15-2 g/L or 0.25-1.9 g/L of the composition. In a particular embodiment, the fucosylated oligosaccharide(s) is/are in a total amount of 1 g/L of the composition. In another particular embodiment, the fucosylated oligosaccharide(s) is/are in a total amount of 0.26 g/L of the composition.

The fucosylated oligosaccharide(s) can be present in the nutritional composition or the growing-up milk in a total amount of 0.004-3.8 g/100 g of composition on a dry weight basis. The fucosylated oligosaccharide(s) may be in a total amount of 0.008-2.3 g/100 g of the composition, such as 0.015-1.5 g/100 g, or 0.08-1.9 g/100 g or 0.12-1.5 g/100 g or 0.15-1.5 g/100 g or 0.19-1.5 g/100 g of the composition. In a particular embodiment, the fucosylated oligosaccharide(s) is/are in a total amount of 0.78 g/100 g of the composition. In another particular embodiment, the fucosylated oligosaccharide(s) is/are in a total amount of 0.2 g/100 g of the composition.

The N-acetylated oligosaccharide(s) can be present in the nutritional composition or the growing-up milk according to the present invention in a total amount of 0.1-3 g/L of the composition. In some embodiments, the N-acetylated oligosaccharide(s) may be in a total amount of 0.01-2.5 g/L of the composition, such as 0.05-1.5 g/L or 0.05-1 g/L or 0.05-0.8 g/L or 0.08-0.8 g/L or 0.09-0.8 g/L of the composition. In a particular embodiment, the N-acetylated oligosaccharide(s) is/are in a total amount of 0.5 g/L of the composition. In another particular embodiment, the N-acetylated oligosaccharide(s) is/are in a total amount of 0.13 g/L of the composition.

The N-acetylated oligosaccharide(s) can be present in the nutritional composition or the growing-up milk in a total amount of 0.008-2.3 g/100 g of composition on a dry weight basis. The N-acetylated oligosaccharide(s) may be in a total amount of 0.008-1.9 g/100 g of composition, such as 0.04-1.2 g/100 g or 0.04-0.8 g/100 g or 0.04-0.6 g/100 g or 0.06-0.6 g/100 g or 0.07-0.6 g/100 g. In a particular embodiment, the N-acetylated oligosaccharide(s) is/are in a total amount of 0.38 g/100 g of the composition. In another particular embodiment, the N-acetylated oligosaccharide(s) is/are in a total amount of 0.1 g/100 g of the composition.

Therefore in one embodiment of the present invention, the nutritional composition or the growing-up milk comprises at least one fucosylated oligosaccharide and at least one N-acetylated oligosaccharide wherein:
    the fucosylated oligosaccharide(s) is/are in a total amount of 0.005-5 g/L of the composition and/or in a total amount of 0.004-3.8 g/100 g of composition on a dry weight basis; and/or
    the N-acetylated oligosaccharide(s) is/are in a total amount of 0.1-2.5 g/L of the composition and/or in a total amount of 0.08-1.9 g/100 g of composition on a dry weight basis.

In another particular embodiment the nutritional composition or the growing-up milk of the present invention comprises at least one fucosylated oligosaccharide and at least one N-acetylated oligosaccharide wherein:
- the fucosylated oligosaccharide(s) is/are in a total amount of 0.005-5 g/L of the composition and/or in a total amount of 0.004-3.8 g/100 g of composition on a dry weight basis; and/or
- the N-acetylated oligosaccharide(s) is/are in a total amount of 0.05-1.5 g/L of the composition and/or in a total amount of 0.04-1.2 g/100 g of composition on a dry weight basis.

In another particular embodiment the nutritional composition or the growing-up milk of the present invention comprises at least one fucosylated oligosaccharide and at least one N-acetylated oligosaccharide wherein:
- the fucosylated oligosaccharide(s) is/are in a total amount of 0.02-2 g/L of the composition and/or in a total amount of 0.015-1.5 g/100 g of composition on a dry weight basis; and/or
- the N-acetylated oligosaccharide(s) is/are in a total amount of 0.5-1 g/L of the composition and/or in a total amount of 0.4-0.8 g/100 g of composition on a dry weight basis.

In another particular embodiment the nutritional composition or the growing-up milk of the present invention comprises at least one fucosylated oligosaccharide and at least one N-acetylated oligosaccharide wherein:
- the fucosylated oligosaccharide(s) is/are in a total amount of 0.1-2.5 g/L of the composition and/or in a total amount of 0.08-1.9 g/100 g of composition on a dry weight basis; and/or
- the N-acetylated oligosaccharide(s) is/are in a total amount of 0.5-0.8 g/L of the composition and/or in a total amount of 0.4-0.6 g/100 g of composition on a dry weight basis.

In a specific embodiment the nutritional composition or the growing-up milk according to the invention comprises at least one fucosylated oligosaccharide and at least one N-acetylated oligosaccharide wherein:
- the fucosylated oligosaccharide(s) is/are in a total amount of 1 g/L of the composition and/or in a total amount of 0.77 g/100 g of composition on a dry weight basis; and/or
- the N-acetylated oligosaccharide(s) is/are in a total amount of 0.5 g/L of the composition and/or in a total amount of 0.38 g/100 g of composition on a dry weight basis.

In another specific embodiment the nutritional composition or the growing-up milk according to the invention comprises at least one fucosylated oligosaccharide and at least one N-acetylated oligosaccharide wherein:
- the fucosylated oligosaccharide(s) is/are in a total amount of 0.26 g/L of the composition and/or in a total amount of 0.2 g/100 g of composition on a dry weight basis; and/or
- the N-acetylated oligosaccharide(s) is/are in a total amount of 0.13 g/L of the composition and/or in a total amount of 0.1 g/100 g of composition on a dry weight basis.

The fucosylated oligosaccharide(s) and the N-acetylated oligosaccharide(s) comprised in the nutritional composition or the growing-up milk according to the invention are typically present in a ratio N-acetylated oligosaccharide(s):fucosylated oligosaccharide(s) of from 1:20 to 2:1, preferably 1:15 to 1:1, most preferably of 1:10 to 1:2. In a particularly advantageous embodiment, this ratio is 1:2 or around 1:2.

In a particular embodiment, the fucosylated oligosaccharide is provided in the nutritional composition or growing-up milk of the present invention in such an amount that normal consumption of the nutritional composition or growing-up milk would provide to the infant or young child, respectively the child, consuming it a total daily dose of 0.003-6.5 g, preferably 0.006-3.9 g, for example 0.012-2.6 g per day.

For preterm, low birth weight and small for gestational age infants, the daily dose of fucosylated oligosaccharides is preferably of 0.05 to 1 g/kg of body weight per day, preferably 0.06-0.9 g or 0.07-0.8 g or 0.08-0.7 g or 0.09-0.6 g or 0.1-0.5 g or 0.2-0.4 g/, most preferably 0.34 g per kg of body weight and per day.

In a particular embodiment, the N-acetylated oligosaccharide is provided in the nutritional composition or growing-up milk of the present invention in such an amount that normal consumption of the nutritional composition or growing-up milk would provide to the infant or young child, respectively the child, consuming it a total daily dose of 0.003-3.9 g, preferably 0.006-3.25 g or 0.03-1.95 g or 0.03-1.3 g or 0.03-1 g, for example 0.05-1 g per day.

For preterm, low birth weight and small for gestational age infants, the daily dose is preferably of 0.005 to 0.1 g/kg of body weight per day, preferably 0.006-0.09 g or 0.007-0.08 g or 0.008-0.07 g or 0.009-0.06 g or 0.01-0.05 g or 0.02-0.04 g/, most preferably 0.034 g per kg of body weight and per day.

The nutritional composition or the growing-up milk according to the present invention may also comprise at least another oligosaccharide(s) (i.e. other than the fucosylated oligosaccharide(s) and N-acetylated oligosaccharide(s) necessarily present in the composition) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose, sialylated oligosaccharides, sialic acid, fucose and any combination thereof. They may be in an amount between 0 and 10% by weight of composition. In a particular embodiment, the nutritional composition or the growing-up milk can also contain at least one BMO (bovine milk oligosaccharide).

Suitable commercial products that can be used in addition to the oligosaccharides comprised in the oligosaccharide mixture to prepare the nutritional compositions or the growing-up milk according to the invention include combinations of FOS with inulin such as the product sold by BENEO under the trademark Orafti, or polydextrose sold by Tate & Lyle under the trademark STA-LITE®.

In a particular embodiment, the nutritional composition or the growing-up milk according to the invention can comprise sialylated oligosaccharide(s). There can be one or several sialylated oligosaccharide(s). The sialylated oligosaccharide(s) can be selected from the group comprising 3' sialyllactose (3-SL), 6' sialyllactose (6-SL), and any combination thereof. In some embodiments of the invention the composition comprises 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10. In some specific embodiments the sialylated oligosaccharide of the composition is 6' sialyllactose (6-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In another preferred embodiment of the invention the nutritional composition or the growing-up milk may comprise from 0.005-5 g/L of sialylated oligosaccharides, or 0.008-2.5 g/L, or 0.01-1 g/L, or 0.02-0.7 g/L, for example 0.03-0.5 g/L.

The nutritional composition or the growing-up milk according to the invention can contain 0.004-3.8 g of sialylated oligosaccharides per 100 g of composition on a dry weight basis, e.g. 0.006-1.9 g or 0.008-0.8 g or 0.015-0.5 g, for example 0.023-0.4 of sialylated oligosaccharides per 100 g of composition on a dry weight basis.

In some particular embodiments of the present invention, the nutritional composition or the growing-up milk comprises sialylated oligosaccharide(s) in an amount of below 0.1 g/100 g of composition on a dry weight basis.

In a particular embodiment, the sialylated oligosaccharide is provided in the nutritional composition or growing-up milk of the present invention in such an amount that normal consumption of the nutritional composition or growing-up milk would provide to the infant or young child, respectively the child, consuming it a total daily dose of 0.003-6.5 g, preferably 0.005-3.3 g or 0.006-1.3 g or 0.01-0.9 g, for example 0.018-0.65 g per day.

In some particular embodiments of the present invention, the nutritional composition or the growing-up milk does not contain any sialylated oligosaccharide(s).

The nutritional composition or the growing-up milk according to the present invention may optionally also comprise at least one precursor of oligosaccharide. There can be one or several precursor(s) of oligosaccharide. For example the precursor of human milk oligosaccharide is sialic acid, fucose or a mixture thereof. In some particular embodiments the composition comprises sialic acid.

In particular examples the nutritional composition or the growing-up milk comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide. The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition or the growing-up milk of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus johnsonii* CNCM I-1225, *Streptococcus salivarius* DSM 13084 sold by BLIS Technologies Limited of New Zealand under the designation K12, *Bifidobacterium lactis* CNCM I-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition or the growing-up milk according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments. Probiotic components and metabolites can also be added.

The nutritional composition according to the invention can be for example an infant formula, a starter infant formula, a follow-on or follow-up formula, a growing-up milk, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses. In such cases it is particularly useful to define the amount of N-acetylated oligosaccharides and optionally other oligosaccharides in terms or daily dose to be administered to the infant or young child, such as described above.

The nutritional composition of the present invention can be in solid (e.g. powder), liquid or gelatinous form.

In a specific embodiment the nutritional composition is a supplement in powder form and provided in a sachet, or in the form of a syrup. When the supplement is in powder form, it may comprise a carrier. It is however preferred that the supplement is devoid of a carrier. When the supplement is in the form of a syrup, the HMOs are preferably dissolved or suspended in water acidified with citrate.

The nutritional composition or the growing-up milk according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids. The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

The protein component can alternatively be replaced by a mixture or synthetic amino acid, for example for preterm or low birth weight infants.

In a particular embodiment the nutritional composition or the growing-up milk according to the invention is a hypoallergenic composition. In another particular embodiment the composition according to the invention is a hypoallergenic nutritional composition or growing-up milk.

The nutritional composition or the growing-up milk according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition or the growing-up milk according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, structured triglyceride oil, high oleic sunflower oil and high oleic safflower oil, medium-chain-triglyceride oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition or the growing-up milk of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition or the growing-up milk of the invention may contain emulsifiers and stabilisers such as soy, lecithin, citric acid esters of mono- and diglycerides, and the like.

The nutritional composition or the growing-up milk of the invention may also contain other substances which may have a beneficial effect such as lactoferrin, nucleotides, nucleosides, and the like.

The nutritional composition or the growing-up milk of the invention may also contain carotenoid(s). In some particular embodiments of the invention, the nutritional composition of the invention does not comprise any carotenoid.

The nutritional composition or the growing-up milk according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm, having a low birth weight and/or born small for gestational age (SGA). In a particular embodiment the nutritional composition of the invention is for use in preterm infants, infants having a low birth weight and/or infants born small for gestational age (SGA).

The nutritional composition of the present invention may also be used in an infant or a young child that was born by C-section or that was vaginally delivered.

In some embodiments the composition according to the invention can be for use before and/or during the weaning period.

The nutritional composition can be administered (or given or fed) at an age and for a period that depends on the needs.

The nutritional composition can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4, 6 or 12 months of birth of said infant. In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

EXAMPLES

The following examples illustrate some specific embodiments of the composition for use according to the present invention. The examples are given solely for the purpose of illustration and are not to be construed as limitations of the present invention.

Example 1

An example of the composition of a nutritional composition (e.g. an infant formula) according to the present invention is given in the below table 1. This composition is given by way of illustration only.

TABLE 1

Composition of the infant formula of Example 1

| Nutrients | | per 100 kcal | per litre |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 11.2 | 74.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (µg) | | 8 | 50 |
| Se (µg) | | 2 | 13 |
| Vitamin A (µg RE) | | 105 | 700 |
| Vitamin D (µg) | | 1.5 | 10 |
| Vitamin E (mg TE) | | 0.8 | 5.4 |
| Vitamin K1 (µg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides | 2FL (g) | 0.15 | 1 |
| (HMOs) | LNnT (g) | 0.075 | 0.5 |

Table 1: an example of the composition of a nutritional composition (e.g. an infant formula) according to the present invention Example 2

Description of the Study

Three groups of time-mated pregnant Sprague-Dawley female rats were bought from Charles River laboratories. One group was submitted to food restriction of 60% during the last 10 days of gestation and their offspring were cross-fostered to normally fed rats. A second group of pregnant females was normally fed and their offspring cross-fostered among the same group of dams. Immediately after birth (d=2), the born rat pups subjects of the experiment—were assigned to one of the following groups:
Normal group (positive control): Normal-weight offspring born from unrestricted dams and fed a normal non-supplemented diet;
IUGR group (negative control; n=20): IUGR rats being fed a normal diet after birth;
IUGR rats+HMO (test groups): During the experiment, they were reared by their mothers for 21 days and supplemented with HMOs (2FL, LNnT or the Mix of 2FL and LNnT). At weaning, they were fed a diet supplemented with the same HMOs, see details below. There were three different groups:
IUGR/2FL group (n=10): supplemented with 2-FL only;
IUGR/LNnT group (n=10): supplemented with LNnT only; and
IUGR/HMOs mix group (n=10): supplemented with LNnT and 2FL in a weight ratio of 1:2.

All rat pups were fed from birth (d=1) up to 57 days (d=57) based on the following protocol:
d1 to d6: all groups of rats were nursed by dam (mothers' milk only);
d7 to d21: all rats were nursed by dam (mothers' milk only). But in the test groups, 3 g/kg body weight of HMO were also administered by gavage:
3 g/kg body weight of 2FL, for the IUGR/2FL group;
3 g/kg body weight of LNnT, for the IUGR/LNnT group;
3 g/kg body weight of a mix of LNnT and 2FL at a 1:2 weight ratio, for the IUGR/HMOs mix group;
d22 to d57: all rats were fed a diet as detailed in Table 2 below.

TABLE 2

Composition of diets fed to the different groups from d22 to d57

| | Amount in diet of Control Group [%] | Amount in diet of 2FL Group [%] | Amount in diet of LNnT Group [%] | Amount in diet of 2FL and LNnT Group [%] |
|---|---|---|---|---|
| Cornstarch | 53.4 | 53.4 | 53.4 | 53.4 |
| Casein | 20 | 20 | 20 | 20 |
| Sucrose | 10 | 10 | 10 | 10 |
| Soybean oil | 7 | 7 | 7 | 7 |
| Mineral Mix AIN-93-G * | 3.5 | 3.5 | 3.5 | 3.5 |
| Choline bitartrate | 0.25 | 0.25 | 0.25 | 0.25 |
| L-Cystine | 0.3 | 0.3 | 0.3 | 0.3 |
| Tert-butylhydroquinone | 0.0014 | 0.0014 | 0.0014 | 0.0014 |
| Vitamin Mix AIN-93-VX * | 1 | 1 | 1 | 1 |
| Maltodextrin | 4.5 | 0 | 0 | 0 |
| 2FL | 0 | 4.5 | 0 | 3 |
| LNnT | 0 | 0 | 4.5 | 1.5 |

* from Research Diets, Inc

Rats were sacrificed at day 57 after a 6-hr fasting period and samples of the small intestine were collected. The length of the villi was measured on a sample of the ileum. One 1-cm sample from the ileum (1 cm cranial from caecum) was collected and flushed with PBS (Sigma D8537). This section was fixed and processed accordingly for histological and morphometric analysis.

Two consecutive 4 µm-thick sections of fixed tissue were stained manually with hematoxylin and eosin to determine villus height. Villus height was captured by light microscopy using a dry 10× objective, using a computerized image analyzer system Axion Vision (version 4.8.2.0, Zeiss®). Ten randomly selected villi were measured in two different segments to determine the mean villi length.

Findings

The length of the villi measured in each rat is represented in FIG. 1. For each group, the mean villi length is represented by a horizontal line. As can be seen, the mean villi lengths of all groups were similar, except for the group that received the combination of 2FL and LNnT, which had significantly longer villi in the ileum. Such increase in the villi length is associated with an increased surface area of the ileum, which provides the rat pups with improved digestion capacity, in particular to digest fats, proteins and carbohydrates. Such improved digestion, in particular fat digestion, is favoured by an improved enterohepatic circulation, in particular the enterohepatic circulation of bile salts, which is associated with the increase surface area of the small intestine, in particular of the ileum.

These results show that a mix of 2FL and of LNnT was successful in increasing the villi length in the ileum of rats having growth retardation (due to the food deprivation of the mothers). The villi of the growth retarded pups fed the diet with 2FL and LNnT were even significantly longer than the villi of the pups that were not faced with intrauterine retarded growth and being fed a normal diet.

These results also show a synergy between 2FL and LNnT, taking into account that neither 2FL, nor LNnT achieved a statistically significant effect when used alone, whereas a statistically significant effect is observed when both are used in combination.

Example 3

A supplement for preterm infants is prepared, such as to provide the following daily dose:
0.034 g/kg of body weight per day of LNnT; and
0.34 g/kg of body weight per day of 2-FL

The invention claimed is:

1. A method of promoting the digestive capacity in an infant or young child in need thereof, the method comprising administering to the infant or young child a nutritional composition comprising at least one N-acetylated oligosaccharide and at least one fucosylated oligosaccharide, wherein the nutritional composition is administered in an effective amount for improving enterohepatic circulation in the infant or young child.

2. The method according to claim 1, for use in the promotion of the capacity to digest fat, liposoluble vitamins, proteins and carbohydrates in the infant or a young child.

3. The method according to claim 1, for promoting the development and/or the growth of the surface area of the small intestine of the infant or young child.

4. The method according to claim 1, for promoting the increase of the villi length in the small intestine of the infant or young child.

5. The method according to claim 1, wherein the N-acetylated oligosaccharide is selected from the group consisting of lacto-N-neotetraose (LNnT), lacto-N-tetraose (LNT), para-lacto-N-neohexaose (para-LNnH), disialyllacto-N-tetraose (DSLNT) and combinations thereof.

6. The method according to claim 5, wherein the N-acetylated oligosaccharide is lacto-N-neotetraose (LNnT).

7. The method according to claim 1, wherein the fucosylated oligosaccharide is selected from the group consisting of 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof.

8. The method according to claim 7, wherein the fucosylated oligosaccharide comprises a 2' fucosyl-epitope.

9. The method according to claim 7, wherein the fucosylated oligosaccharide is 2'-fucosyllactose (2'FL).

10. The method according to claim 1, comprising 2'-fucosyllactose and lacto-N-neotetraose (LNnT), or comprising an oligosaccharide mixture consisting of 2'-fucosyllactose (2'FL) and lacto-N-neotetraose (LNnT).

11. The method according to claim 1, wherein the N-acetylated oligosaccharide and the fucosylated oligosaccharide are present in a ratio N-acetylated oligosaccharide(s):fucosylated oligosaccharide(s) of from 1:20 to 2:1.

12. The method according to claim 1, wherein
a. the fucosylated oligosaccharide(s) is/are in a total amount of 0.005-5 g/L of the composition and/or in a total amount of 0.004-3.8 g/100 g of composition on a dry weight basis; and/or
b. the N-acetylated oligosaccharide(s) is/are in a total amount of 0.1-2.5 g/L of the composition and/or in a total amount of 0.08-1.9 g/100 g of composition on a dry weight basis.

13. The method according to claim 1, wherein
a. the fucosylated oligosaccharide(s) is/are in a total amount of 0.02-2 g/L of the composition and/or in a total amount of 0.015-1.5 g/100 g of composition on a dry weight basis; and/or
b. the N-acetylated oligosaccharide(s) is/are in a total amount of 0.5-1 g/L of the composition and/or in a total amount of 0.4-0.8 g/100 g of composition on a dry weight basis.

14. The method according to claim 1, wherein
a. the fucosylated oligosaccharide(s) is/are in a total amount of 0.1-2.5 g/L of the composition and/or in a total amount of 0.08-1.9 g/100 g of composition on a dry weight basis; and/or
b. the N-acetylated oligosaccharide(s) is/are in a total amount of 0.5-0.8 g/L of the composition and/or in a total amount of 0.4-0.6 g/100 g of composition on a dry weight basis.

15. The method according to claim 1, comprising at least another oligosaccharide(s) and/or fiber(s) and/or precursor(s) thereof selected from the group consisting of galacto-oligosaccharides (GOS), fructo-oligosaccharides (FOS), xylooligosaccharides (XOS), inulin, polydextrose, sialylated oligosaccharides, sialic acid, fucose and any combination thereof.

16. The method according to claim 1, the composition further comprising at least one probiotic in an amount of from $10^3$ to $10^{12}$ cfu/g of the composition (dry weight).

17. The method according to claim 1, wherein the nutritional composition is selected from the group consisting of an infant formula, a starter infant formula, a follow-on or follow-up infant formula, a growing-up milk, a baby food, an infant cereal composition, a fortifier or a supplement.

18. The method according to claim 1, wherein the infant or young child is a preterm infant, an infant having a low birth weight, an infant born small for gestational age (SGA) and/or a growth-retarded infant or young child.

19. The method according to claim 18, wherein the infant is an IUGR infant.

* * * * *